US009110023B2

(12) United States Patent
Gao (10) Patent No.: US 9,110,023 B2
(45) Date of Patent: Aug. 18, 2015

(54) OPTICAL SYSTEM (75) Inventor: Songping Gao, Ashland, MA (US)

(73) Assignee: Analogic Corporation, Peabody, MA (US)

(*) Notice: Subject to any disclaimer, the term of this patent is extended or adjusted under 35 U.S.C. 154(b) by 708 days.

(21) Appl. No.: 13/239,758

(22) Filed: Sep. 22, 2011

(65) Prior Publication Data

US 2013/0075626 A1    Mar. 28, 2013

(51) Int. Cl.
*G01J 1/00* (2006.01)
*G01N 21/64* (2006.01)

(52) U.S. Cl.
CPC ............ *G01N 21/64* (2013.01); *G01N 21/6428* (2013.01); *G01N 2021/6439* (2013.01); *G01N 2201/12723* (2013.01)

(58) Field of Classification Search
CPC .......... G01N 2021/6439; G01N 21/64; G01N 21/6428; G01N 2201/1273
USPC .......................................................... 356/213
See application file for complete search history.

(56) References Cited

U.S. PATENT DOCUMENTS 6,075,613 A * 6/2000 Schermer et al. ............. 356/446
2007/0167835 A1* 7/2007 Yu et al. ........................ 600/476

OTHER PUBLICATIONS

Goodwin et al. (P.M. Goodwin, W. P. Ambrose, J.C. Martin, and R.A. Keller, "Spatial dependence of the optical collection efficiency in flow cytometry," Cytometry 21, 133-144 (1995)).*
Jorg Enderlein and W. Patrick Ambrose, "Optical collection efficiency function in single-molecule detection experiments" Applied Optics, vol. 36, No. 22, Aug. 1, 1997, pp. 5298-5302.*

* cited by examiner

*Primary Examiner* — Michael A Lyons
*Assistant Examiner* — Shawn Decenzo
(74) *Attorney, Agent, or Firm* — Anthony M. Del Zoppo, III; Driggs, hogg, Daugherty & Del Zoppo Co., LPA (57) ABSTRACT

An optical system includes a sample carrier receiving region configured to receive a carrier carrying a sample for processing, a source that emits an excitation signal having a wavelength within a first predetermined wavelength range, and a first set of optical components that direct the excitation signal along an excitation path to the sample carrier receiving region, wherein radiation having a wavelength within a second predetermined wavelength range is emitted from the sample carrier receiving region in response to receiving the excitation signal. The system further includes a detector configured to detect the emitted radiation and generates a signal indicative of a power of the detected radiation and a second set of optical components that directs the emitted radiation along a collection path to the detector and a power meter that measures a power of the radiation emitted from the sample carrier receiving region and generates a signal indicative thereof.

10 Claims, 8 Drawing Sheets

OPTICAL SYSTEM

TECHNICAL FIELD

The following generally relates to an optical system and is described with particular application to an apparatus configured to process DNA samples. However, the following is also amenable to other DNA and/or non-DNA sample processing applications.

BACKGROUND

A micro-channel device includes one or more micro channels through which one or more small volumes of samples are routed for processing and/or analysis. An example of such a device includes a sample carrier such as a biochip, a lab-on-a-chip, and/or other micro-channel device. An application in which a micro-channel device has been used is DNA sequencing. DNA sequencing, generally, is a method for determining an order of the nucleotide bases (i.e., adenine, guanine, cytosine, and thymine) of DNA in a sample.

For DNA sequencing, DNA in a sample is lysed, producing DNA fragments of sequences of the four nucleotides. The fragments are replicated through polymerase chain reaction (PCR) and labeled with target specific fluorescent dyes (e.g., one for each nucleotide base), each dye having its own fluorescent emission characteristic (e.g., wavelength, frequency, energy and color). The labeled fragments are separated by size through electrophoresis.

An optical system is used to illuminate the separated fragments with an excitation signal. The excitation signal is absorbed by the dyes of the fragments, and the dyes fluoresce based on their respective fluorescent emission characteristics. The optical system detects the fluorescent emission and generates signals indicative thereof. The signals are processed to identify the nucleotides of and sequence the DNA.

Generally, when an optical system is installed in a DNA sequencer, an optical performance of the installed optical system is not known, and the performance thereof may not satisfy given performance criteria, for example, due to optical misalignment, mismatched optical components, etc. In view of the foregoing, there is an unresolved need to determine an optical performance of the optical system installed in a DNA sequencer.

SUMMARY

Aspects of the application address the above matters, and others.

In one aspect, an optical system includes a sample carrier receiving region configured to receive a sample carrier carrying a sample for processing, a source that emits an excitation signal having a wavelength within a first predetermined wavelength range, and a first set of optical components that direct the excitation signal along an excitation path to the sample carrier receiving region, wherein radiation having a wavelength within a second predetermined wavelength range is emitted from the sample carrier receiving region in response to receiving the excitation signal. The optical system further includes a detector configured to detect the emitted radiation and generates a signal indicative of a power of the detected radiation and a second set of optical components that directs the emitted radiation along a collection path to the detector. The optical system further includes a power meter that measures a power of the radiation emitted from the sample carrier receiving region and generates a signal indicative thereof.

In another aspect, a method of determining an optical performance of an optical system includes measuring a signal power of a signal emitted from a sample carrier receiving region and traversing a collection path to a detector, measuring a signal power of the signal received at the detector, wherein the emitted signal traverses at least one optical component while traversing the collection path between the sample carrier receiving region and the detector, and generating a signal indicative of an optical collection efficiency based on a ratio of the signal power of the signal emitted received at the detector to the signal power of a signal emitted from a sample carrier receiving region.

In another aspect, a method of determining an optical performance of an optical system includes measuring a signal power of a signal emitted by a source, measuring a signal power of the emitted signal received at a sample carrier receiving region, wherein the emitted signal traverses at least one optical component while traversing an excitation path between the source and the sample carrier receiving region, and generating a signal indicative of an optical excitation efficiency based on a ratio of the signal power of the signal emitted received at the sample carrier receiving region to the signal power of the signal emitted by the source.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
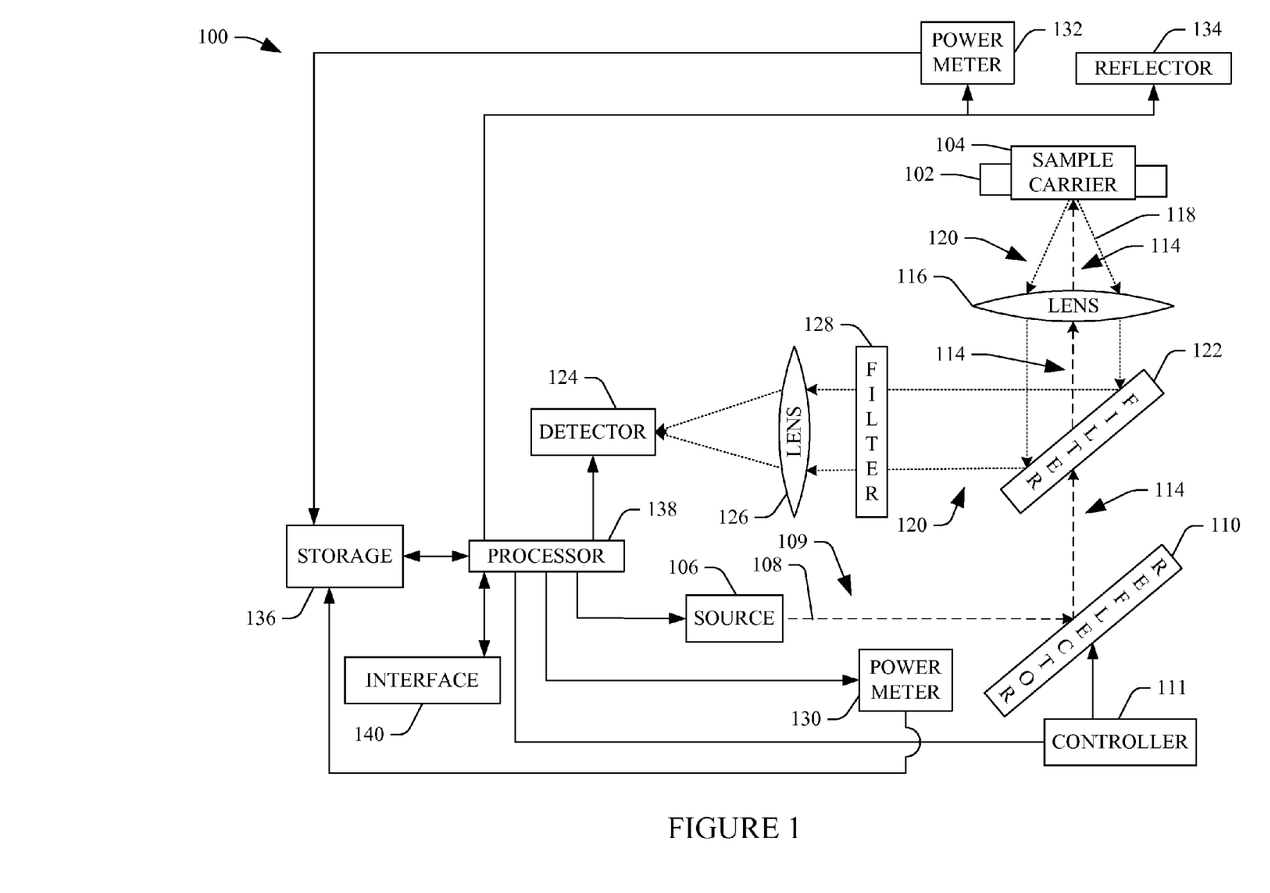
FIG. 1 schematically illustrates an example optical system.

FIG. 1 illustrates an example optical system 100. The optical detection system 100 may be a stand alone system or part of another system such as a sample processor and/or analyzer, including, but not limited to, an apparatus configured to sequence and/or otherwise process DNA and/or other apparatus.

The optical detection system 100 includes a sample carrier support region 102, which is configured to receive and support a sample carrier 104 for processing sample carried thereby, a power meter (e.g., FIG. 4), a reflector (e.g., FIG. 6), a source (e.g., FIG. 8), and/or other component. Examples of a suitable sample carrier include, but are not limited to, micro-channel devices such as a lab-on-a-chip (LOC), a biochip, micro-fluidic arrays, and/or other micro-channel devices and/ or sample carriers. The illustrated sample carrier 104 is configured to carry one or more samples for processing in one or more processing channels of the sample carrier.

A non-limiting example of a suitable sample includes a bio-sample such as one or more labeled DNA fragments and/or other sample. A suitable label includes a fluorescent or other material that absorbs incident excitation electromagnetic radiation and emits a corresponding characteristic signal. In the context of DNA analysis, the label may include at least four different fluorescent dyes, each dye being target specific, binding to a different one of the four nucleotide bases (adenine (A), guanine (G), cytosine (C), and thymine (T)), and fluorescing characteristic radiation. One or more other dyes may also be included. For example, a calibration dye may also be included.

An electromagnetic radiation source (source) 106 generates and transmits an excitation signal 108 (electromagnetic radiation) along a transmission path 109. An example of a suitable source 106 is a laser that transmits within a known electromagnetic radiation range. For example, the illustrated system includes a narrow beam (e.g., 10 to 100 micron diameter) 488 nanometer (±5 nm) 200 (~160) milliwatt laser. Other wavelengths (e.g., >500 nm such at 560 nm) and/or other sources, including non-laser sources such as a light emitting diode (LED), an incandescent light, etc. are also contemplated herein.

A beam reflector 110 such as a mirror or other reflector directs the transmitted signal 108 along an excitation path 114 from the reflector 110 to the sample carrier support region 102. The reflector 110 is movably mounted and is configured to rotate, pivot or tilt to scan the excitation path 114 and hence the excitation signal 109 across the sample carrier 104. In one instance, the reflector 110 is movably mounted on an end of a rotary shaft of a closed loop Galvanometer. A controller 111 controls the Galvanometer to rotate, pivot or tilt the reflector 110 to move the signal 108.

A lens 116 is disposed between the sample carrier support region 102 and the reflector 110 in the transmission path 114 and is configured to focus the excitation signal 108, for example, at a component such as the sample carrier 104 (as shown) installed in the sample support region 102. The lens 116 also focuses radiation 118 emitted from the component installed in the sample carrier support region 102 along a collection path 120. The illustrated lens 116 includes a biconvex lens. However, other lenses such as a plano-convex or other lens are also contemplated herein. Moreover, the lens 116 may include more than one lens, or may be omitted.

A filter 122 is disposed between the reflector 110 and the lens 116 in the transmission and collection paths 114 and 120. The filter 122 filters radiation traversing the transmission and collection paths 114 and 120 such that only substantially all of the excitation radiation 108 passes and only substantially all of the emitted radiation 120 is reflected. An example of a suitable filter includes a dichroic filter, band-pass filter, or other filter that selectively passes and/or filters electromagnetic radiation.

An optical detector 124 detects electromagnetic radiation traversing the collection path 120 and generates a signal indicative thereof. The detector 124 may include a photomultiplier tube (PMT), a charge-coupled device (CCD) camera, or the like, and may be tunable or fixed. The detector 124 may include one or more sub-detectors, each configured to detect different bands of radiation within a range of interest.

A lens 126, disposed between the filter 122 and the detector 124, focuses the radiation traversing the collection path 120. Similar to the lens 116, the lens 126 includes a biconvex lens, but additionally or alternatively can include other lenses such as a plano-convex or other lens that suitably focuses the radiation with respect to the detector 124.

A filter 128, disposed between the lens 126 and the filter 122, pass radiation traversing the collection path 120 that has spectral characteristics within a predetermined spectral characteristic range of interest and attenuate and/or reflect other unwanted electromagnetic radiations. The lens 128 may include more than one lens or may be omitted.

A power meter 130 is configured to move between at least a first position (shown) in which the power meter 130 is outside of the transmission path 108 and a second position (shown) in which the power meter 130 is in the transmission path 108. A power meter 132 is configured to move between at least a first position (shown) in which the power meter 132 is outside of the excitation path 114 and a second position in which the power meter 132 is in the excitation path 114 at the sample carrier support region 102. Known and/or other drive systems, including, but not limited to a controller, a motor, a drive, etc. can be utilized to move the power meters 130 and 132 through there respective positions.

The power meter 130 detects a power of the excitation signal 108 traversing the transmission path 109 and generate a signal indicative thereof, and the power meter 132 detects a power of the excitation signal 108 received at the sample carrier receiving region 102 and generate a signal indicative thereof. In another embodiment, the same power meter is used for both of the power meters 130 and 132. In this instance, the shared power meter is configured to move between the different location in the transmission and excitation paths 109 and 120. In yet another embodiment, at least one of the power meters 130 and 132 is configured to be removeably affixed to a static position. In this instance, the at least one of the power meters 130 and 132 affixed in the static position to measure power and not affixed or removed from the system 100 to process samples.

A reflector 134 is also configured to move between at least a first position (shown) in which the reflector 134 is outside of the excitation path 114 and a second position in which the power meter 132 is in the excitation path 114 at the sample carrier support region 102. The reflector 134, when in the second position, reflects the excitation signal received at the sample carrier receiving region 102 into the collection path 120. As such, the reflected signal can be considered as a signal emitted from the sample carrier support region 102 and has a power substantially similar to the incident excitation signal, or the power of the excitation signal less any power losses for the reflector 134. Similar to the power meters 130 and 132, known and/or other drive systems, including, but not limited to a controller, a motor, a drive, etc. can be utilized to move the reflector 134 through its respective positions, or, alternatively, the reflector 134 is configured to be removeably affixed to a static position to measure power and not affixed or removed from the system 100 to process samples.

Storage 136, such as physical memory, is used to store computer readable and/or executable information local to the system 100. In one instance, the information includes instructions for controlling (e.g., moving, activating, deactivating, etc.) the power meters 130 and 132, and for controlling (e.g., moving, etc.) the reflector 134. Additionally or alternatively, the information includes the signals generated by the power meters 130 and 132. Additionally or alternatively, the information includes one or more algorithms for processing the signals. Additionally or alternatively, the information includes manufacturer optical specifications for various components of the system 100.

For example, the information can include the output power characteristics of the source 106, transmittance and/or reflectance properties of the reflectors 110 and 134, the filters 122 and 128, the lenses 116 and 126, and/or other components. Additionally or alternatively, the information includes one or more algorithms for processing the information stored therein, and, optionally, criteria for analyzing the processed signals along with the processed information. As described in greater detail below, such algorithms may include instructions at least for determining an optical performance (e.g., excitation efficiency, collection efficiency, etc.) from the signals and theoretically, and/or analyzing such performance metrics based on predetermined optical performance criteria.

A processor 138 controls the various components of the system 100, including, but not limited to, the source 106, the controller 111, the detector 124, the power meter 130, the power meter 132, the power meter drive systems (where applicable), the reflector 134, the reflector drive systems (where applicable), etc. The processor 138 also executes the algorithms in the storage and/or analyzes results produced by executing the algorithms. For example, the processor 138 can calculate one or more the optical performance metrics and/or analyze such metrics. The processor 138 executes instructions stored on the storage 136. The processor 138 can additionally or alternatively execute instructions carried by a carrier wave, signal, or other non-computer readable storage medium.

An interface 140, in operative communication with at least the processor 138, includes one or more input and/or one or more output devices. Examples of suitable input devices include a touch screen, buttons, knobs, etc. which allow a user to operate the system 100, for example, to select a mode of operation, initiate the execution of performance algorithms stored in the storage 136, initiate sample processing, and/or other input devices. Examples of suitable output devices include a display screen, visual and/or audible indicators (e.g., lights, sound, etc.), one or more communication ports for communicating with another device and/or a network, and/or other output devices. Examples of information that can be presented to a user and/or conveyed to another device via the interface 140 include, but are not limited to, the optical performance and/or indicia indicative thereof.

As briefly discussed above, the storage 136 can include various algorithms for determining an optical performance of the system 100. The following provides a non-limiting example of suitable algorithms.

In one instance, the algorithms include instructions at least for determining an optical excitation efficiency (OEE) and/or an optical collection efficiency (OCE), both theoretically and from measurements. In this example, the OEE is calculated as a ratio of a power of the excitation signal received at the sample carrier 104 ($I_{sc}$) to a power of the excitation signal emitted by the source 106 ($I_o$), and the OCE is calculated as a ratio of a power of the signal collected by the detector 124 ($I_D$) to a power of the signal emitted from the sample carrier 104 ($I_{sc}$).

For the theoretical determination, the output power of the source 106 can be obtained from the manufacturer (e.g., a product specification data sheet, etc.) and/or other source and used for the $I_o$. The $I_{sc}$ can be calculated based on the $I_o$ and the optical parameters of the optical components in the paths 109 and 114 between the source 106 and the sample carrier support region 102. In one instance, this includes reflectance (R) and/or transmittance (T) of any reflectors, filters, lenses, etc. in the paths 109 and 114, such as the reflector 110, the filter 122, and the lens 116 in FIG. 1.

For example, for the embodiment illustrated in FIG. 1, $I_{sc}$ can be calculated as shown in Equation 1:

$$I_{sc} = I_o \times R_{110} \times T_{112} \times T_{116}, \text{ and} \qquad \text{Equation: 1}$$

OEE can be calculated as shown in Equation 2:

$$OEE = I_{sc}/I_o = R_{110} \times T_{112} \times T_{116}. \qquad \text{Equation 2:}$$

Generally, the illustrated reflector 110 has a broadband coating and the lens 116 is Achromatic, and, thus, the reflectance (R) and/or transmittance (T) of the reflector 110 and the lens 116 is the same across the visible light wavelength range. As such, the reflectance (R) and/or transmittance (T) of the reflector 110 and the lens 116 is the same for other excitation signal in the visible light range. However, the transmittance (T) of the filter 122 is a function of the wavelength of the excitation signal. In this example, the transmittance (T) of the reflector 116 is such that substantially all of the excitation signal passes through the filter 122 so a level of the signal reflected along the collection path 120 to the detector 124 should be relatively small. For different excitation signal wavelengths, different filters 122 can be used.

The $I_D$ can be calculated based on the $I_{sc}$ and the optical parameters of the optical components in the path 120 between the sample support region 102 and the detector 124. Likewise, this includes the reflectance (R) and/or the transmittance (T) of any reflectors, filters, lenses, etc. in the path 120, such as the lens 116, the filter 122, the filter 128, and the lens 126 in FIG. 1. For example, for the embodiment illustrated in FIG. 1, $I_D$ can be calculated as shown in Equation 3:

$$I_D = I_{sc} \times T_{116} \times R_{122} \times T_{128} \times T_{126}, \text{ and} \qquad \text{Equation 3:}$$

OCE can be calculated as shown in Equation 4:

$$OCE = I_D/I_{sc} = T_{116} \times R_{122} \times T_{128} \times T_{126}. \qquad \text{Equation 4:}$$

Alternatively, where a second source with known output power ($I_{o2}$) is positioned at the sample support region 102, the $I_{o2}$ is used in place of $I_{sc}$.

Likewise, the illustrated lenses 116 and 126 are Achromatic, and, thus, the transmittance (T) thereof is the same across the visible light wavelength range. As such, the transmittance (T) of the lenses 116 and 126 are the same for other signals in the visible light range traversing the collection path 120. However, the transmittance (T) of the filters 122 and 128 is a function of the wavelength of the signal traversing the collection path 120. In this example, the transmittance (T) of the filter 122 is such that all or substantially all of the excitation signal passes through the filter 122, and a signal having a wavelength of interest (such as a wavelength corresponding to a wavelength detected by the detector 124) is reflected and remains in the collection path 120. The filter 128 passes the signal having a wavelength of interest and filters other signals traversing the collection path 120.

Generally, the $I_o$ and the transmittance (T) and reflectance (R) parameters are provided by the manufacturer and/or other source, for example, in an electronically formatted or other product specification sheet and/or other document. In one instance, this data can be stored in the storage 136 as part of the information stored therein. In another instance, this information is additionally or alternatively stored in storage remote from the system 100, for example, in connection with a computing device such as a computer or other computing device.

For the determination of the OEE and OCE based on measurements, the signal generated by the power meter 130 corresponds to the power of the excitation signal 108 ($I_o$), the signal generated by the detector 124 corresponds to the power of the collected signal ($I_D$), and the signal generated by the power meter 132 corresponds to both or either the power of the excitation signal received at the sample carrier 104 ($I_{sc}$) and/or the signal emitted from the sample carrier 104 ($I_{sc}$).

The algorithms may also include instructions at least determining an optical excitation performance (OEP) and an optical collection performance (OCP) based on the OEEs and the OCEs. In one instance, the OEP is determined based on a difference between the theoretical and the measurement based OEEs as shown in Equation 5:

$$OEP = OEE_{experimental} - OEE_{theoretical}, \quad \text{Equation 5:}$$

which can be compared against a predetermined threshold to determine whether OEP of the system 100 satisfies predetermined performance criteria. For example, in one instance, where OEP≥Threshold, the OEP is deemed to satisfy the predetermined performance criteria, and where OEP<Threshold, the OEP is deemed to not satisfy the predetermined performance criteria.

Likewise, the OCP can be determined based on a difference between the theoretical and the experimental OCEs as shown in Equation 6:

$$OCP = OCE_{experimental} - OCE_{theoretical}, \quad \text{Equation 6:}$$

which can be compared against a predetermined threshold to determine whether OCP of the system 100 satisfies predetermined performance criteria. For example, in one instance, where OCP≥Threshold, the OCP is deemed to satisfy the predetermined performance criteria, and where OCP<Threshold, the OCP is deemed to not satisfy the predetermined performance criteria.

The OEP and/or the OCP can be determined and/or analyzed via the processor 138 of the system 100 and/or a processor remote from the system 100.

Figure 2:
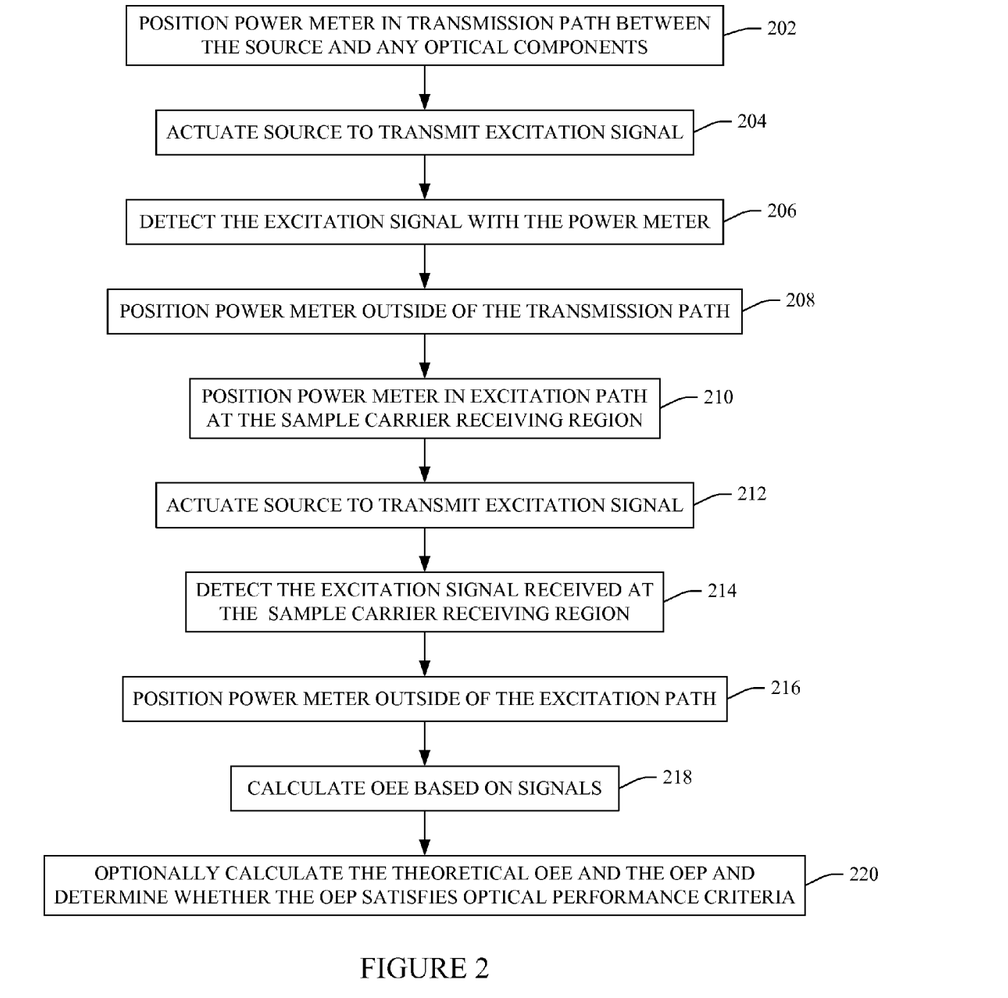
FIG. 2 illustrates an example method for determining an optical excitation efficiency of the optical system of FIG. 1.
Figure 3:
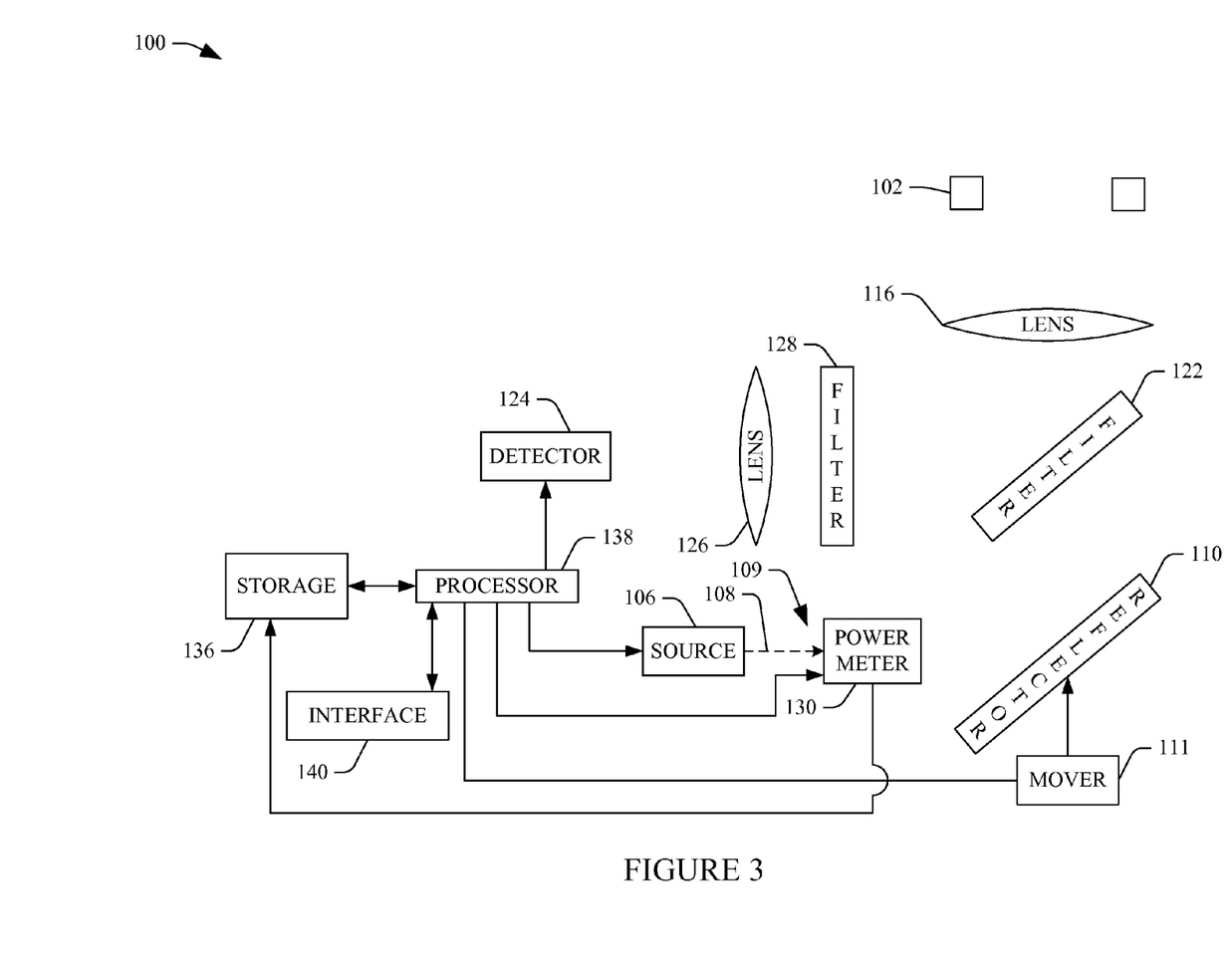
FIG. 3 illustrates the system of FIG. 1 in a configuration for measuring excitation signal power.
Figure 4:
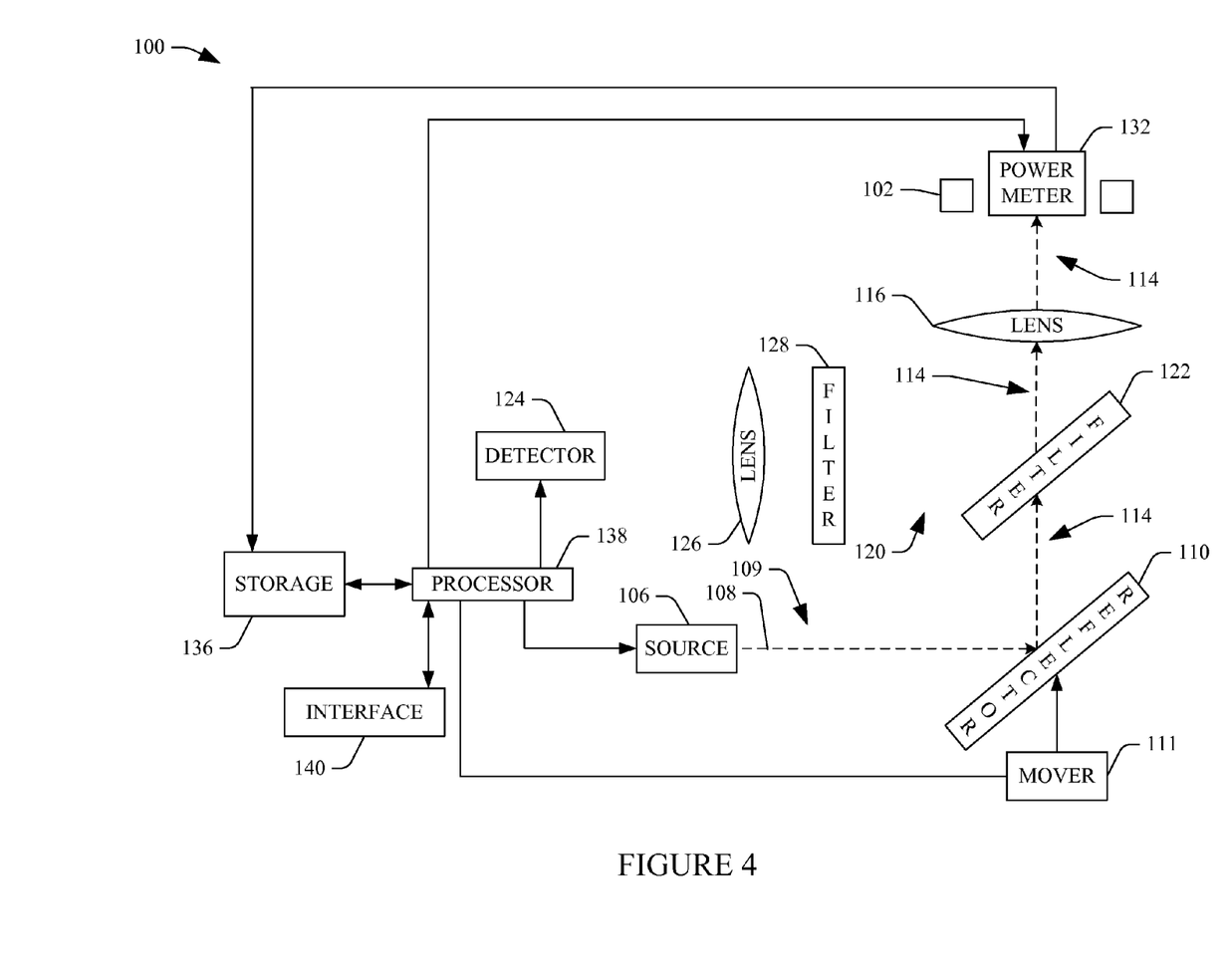
FIG. 4 illustrates the system of FIG. 1 in a configuration for measuring the power of the excitation signal received at and/or a signal emitted from the sample carrier receiving region of the system.

FIGS. 2, 3 and 4 illustrate a method for determining an optical excitation efficiency (OEE) of the system 100 with the signals generated by the power meters 130 and 132.

Note that the acts described below are not limiting. As such, one or more acts may be added and/or one or more acts may be omitted, and the ordering of the acts may be different, including having concurrent acts.

Initially referring to FIG. 2, at 202, the power meter 130 is positioned in the transmission path 109. FIG. 3 shows the power meter 130 in this position. For sake of clarity, the power meter 132 and the reflector 134 are omitted in FIG. 3.

Returning to FIG. 2, at 204, the source 106 is actuated to transmit the excitation signal 108.

At 206, the power meter 130 detects the excitation signal 108 in the transmission path 109, generates an electrical signal indicative thereof, and conveys the signal to the storage 136.

At 208, the power meter 130 is positioned out of the transmission path 109.

At 210, the power meter 132 is positioned in the excitation path 114 at the sample carrier support region 102. FIG. 4 shows the power meter 132 in this position. For sake of clarity, the power meter 130 and the reflector 134 are omitted in FIG. 4.

Returning to FIG. 2, at 212, the source 106 transmits the excitation signal 108.

At 214, the power meter 132 detects the transmitted excitation signal 114 at the sample receiving region 102, generates an electrical signal indicative thereof, and conveys the signal to the storage 136.

At 216, the power meter 132 is positioned out of the excitation path 114.

At 218, an OEE is calculated based on the signals, as discussed herein and/or otherwise.

At 220, optionally, a theoretical OEE is calculated, an OEP is calculated, and the OEP is compared against an optical threshold to determine whether the OEP satisfies the threshold.

Figure 5:
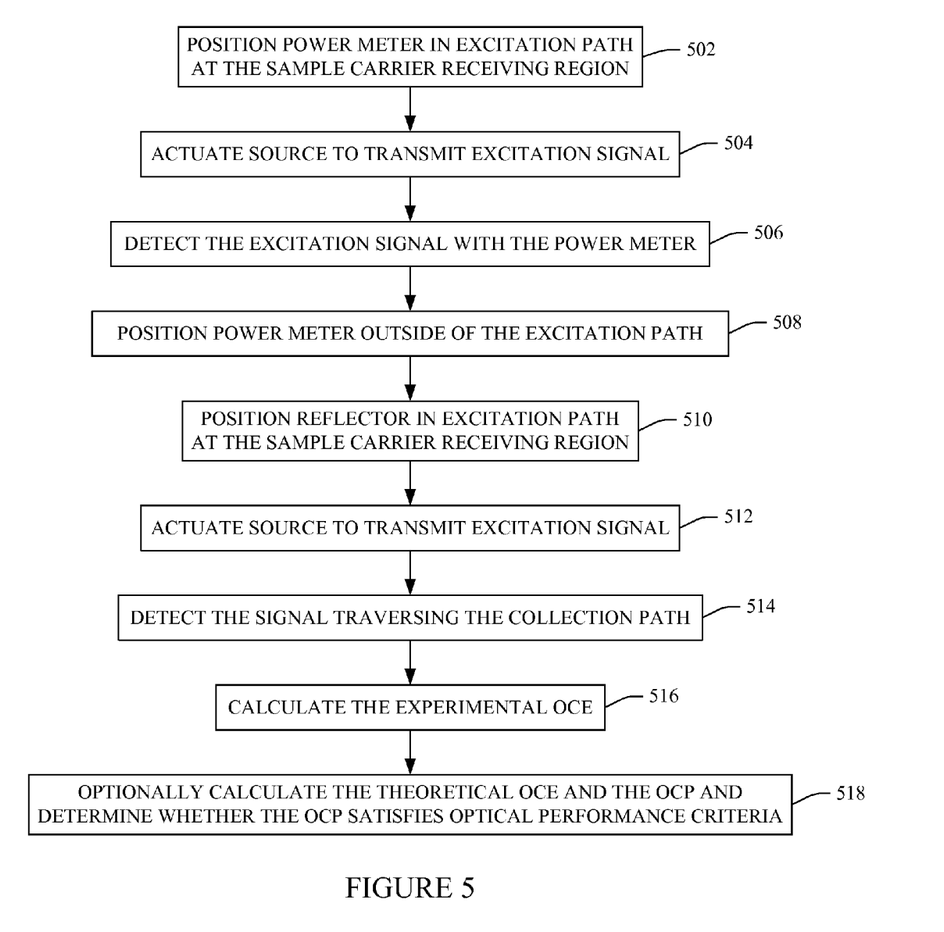
FIG. 5 illustrates an example method for determining an optical collection efficiency of the optical system of FIG. 1.
Figure 6:
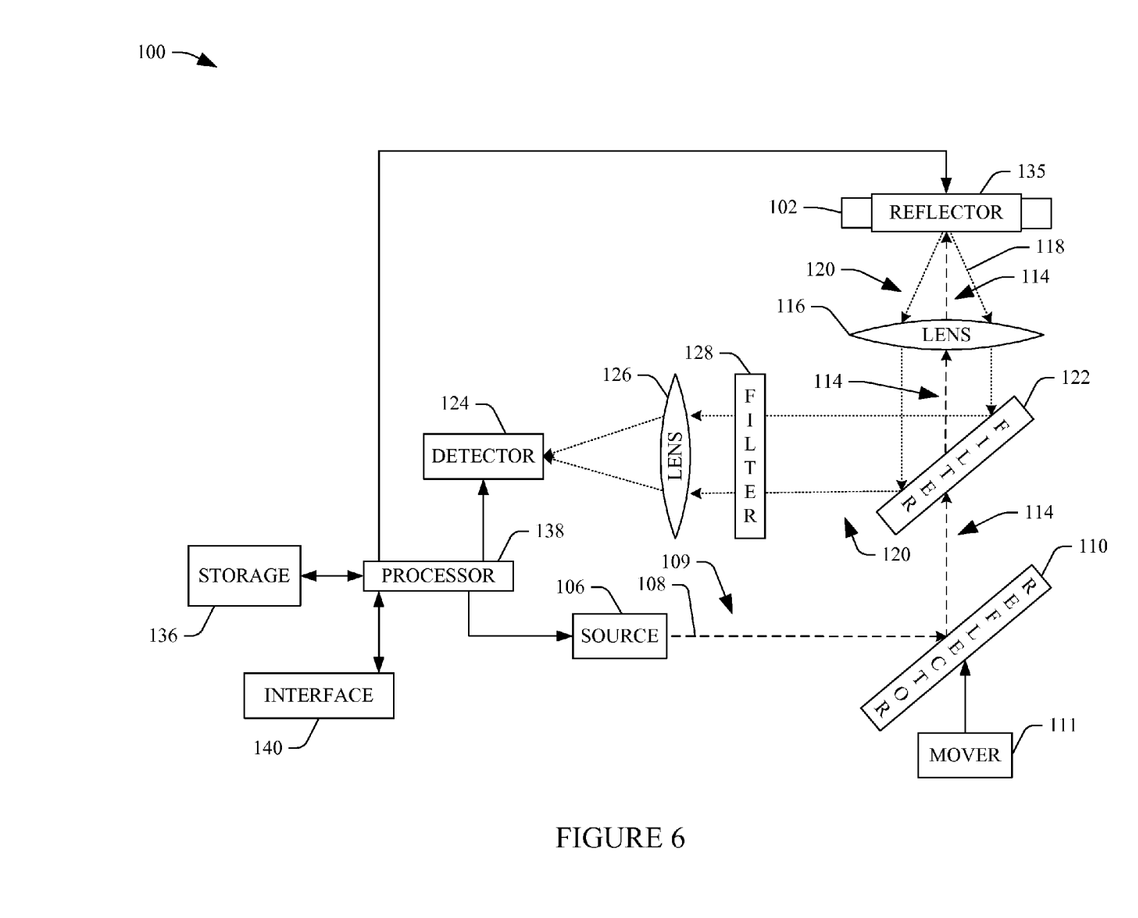
FIG. 6 illustrates the system of FIG. 1 in a configuration for measuring the power of the signal received at the detector of the system.

FIGS. 4, 5 and 6 illustrate a method for determining an optical collection efficiency (OCE) of the system 100, with the signals generated by the power meters 132 and 134.

Note that the acts described below are not limiting. As such, one or more acts may be added and/or one or more acts may be omitted, and the ordering of the acts may be different, including having concurrent acts.

Initially referring to FIG. 5, at 502, the power meter 132 is positioned in the excitation path 114 at the sample carrier receiving region 102. FIG. 4 shows the power meter 132 in this position. For sake of clarity, the power meter 130 and the reflector 134 are omitted in FIG. 4.

Returning to FIG. 5, at 504, the source 106 transmits the excitation signal 108. At 506, the power meter 132 detects the excitation signal 114 received at the sample receiving region 102, generates an electrical signal indicative thereof, and conveys the signal to the storage 136.

At 508, the power meter 132 is positioned out of the excitation path 114.

Returning to FIG. 5, at 510, the reflector 134 is positioned in the excitation path 114 at the sample support receiving region 102. FIG. 6 shows the reflector 135 in this position.

At 512, the source 106 is activated to transmit the excitation signal 108, which traverses the excitation path 114 to the sample carrier receiving region 102 and is reflected into the collection path 120.

At 514, the detector 124 detects the signal traversing the collection path 120, generates an electrical signal indicative thereof, and conveys the signal to the storage 136.

At 516, an OCE is calculated based on the signals as described herein and/or otherwise.

At 518, optionally, a theoretical OCE is calculated, an OCP is calculated, and the OCP is compared against an optical threshold to determine whether the OCP satisfies the threshold.

It is to be appreciated that the above acts may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

Figure 7:
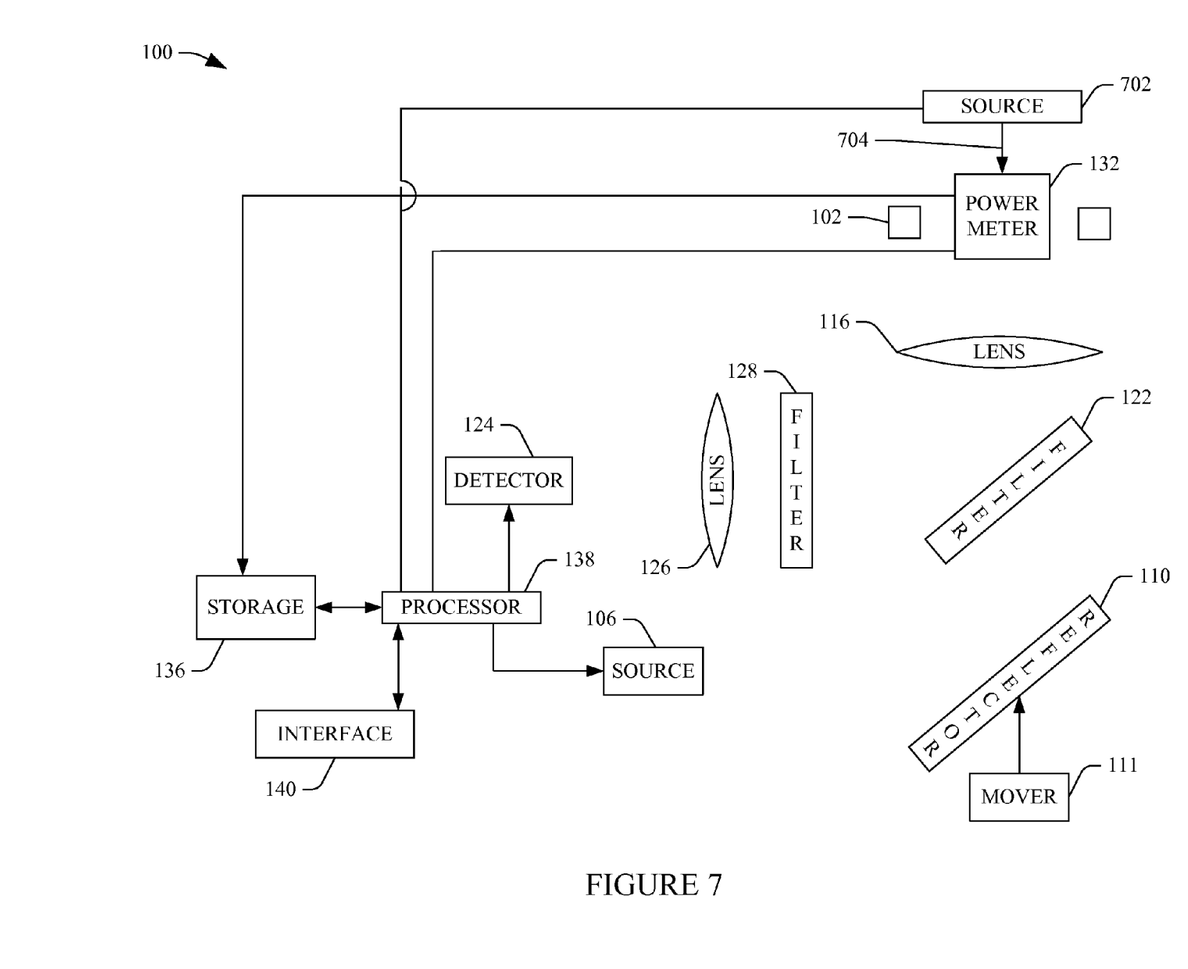
FIG. 7 illustrates a variation of the optical system of FIG. 1 in a configuration for measuring the power of the signal emitted from the sample carrier receiving region.
Figure 8:
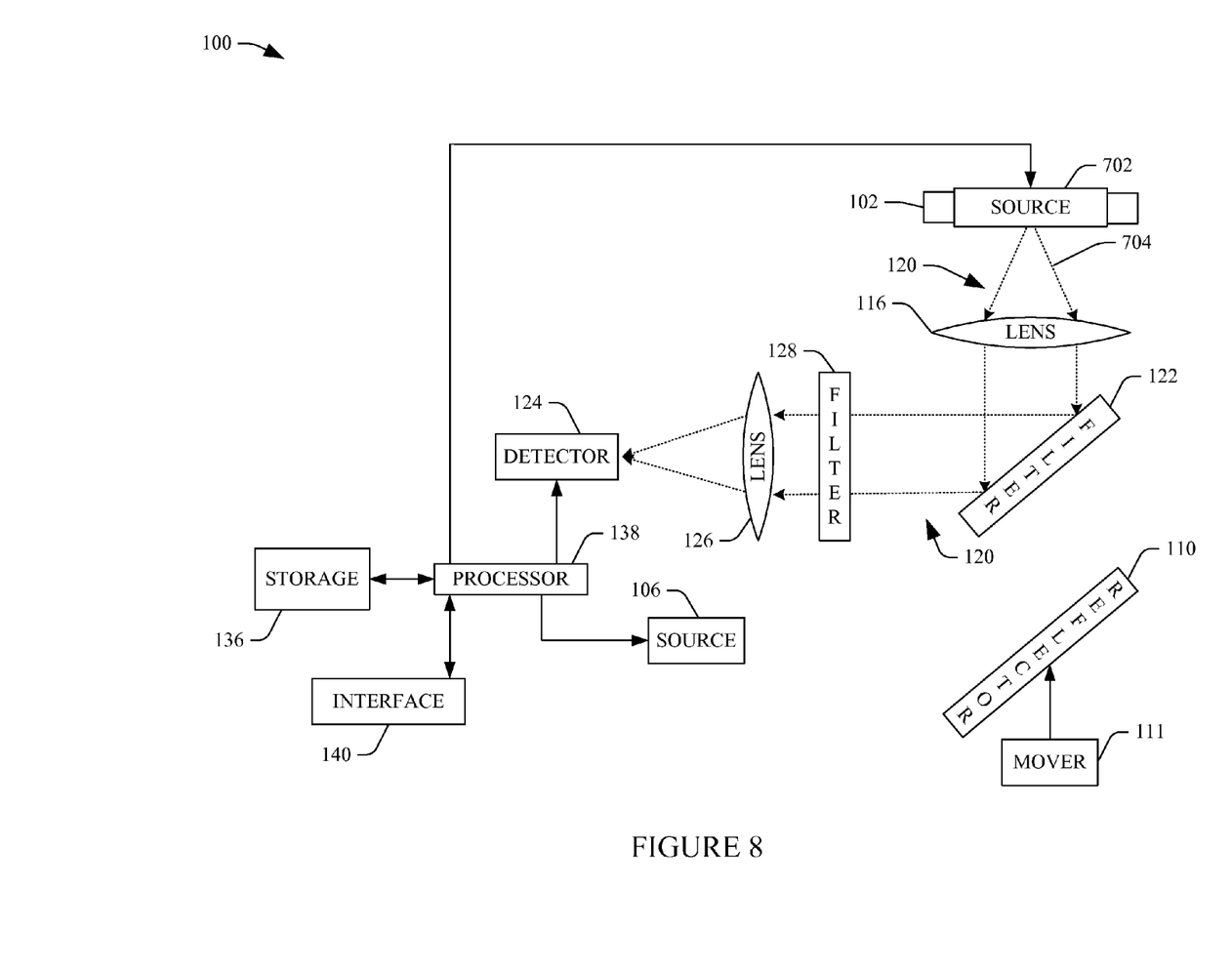
FIG. 8 illustrates the variation of FIG. 7 in a configuration for measuring the power of the signal received at the detector of the system.

FIGS. 7 and 8 illustrate a variation in which a second source 702 is positioned at the sample carrier receiving region 102 for determining the OCE instead of using a reflected excitation signal 108. As shown in FIG. 7, the power meter 132 is used to measure a power of a signal 704 emitted by the second source 702, and as shown in FIG. 8, the second source 702 emits the signal 704, which traverses the collection path 120 and is received by the detector 124.

In this instance, the second source 702 transmits electromagnetic radiation having a wavelength outside of that which is passed by (but which is reflected by) the filter 122 and within that which is passed through the filter 128, such as a wavelength greater than 500 nm such as 560 nm. Since the filter 122 reflects all or substantially all of the signal 704, the signal level detected by the detector 124 will be greater than that with the embodiment of FIG. 6 in which the excitation signal 108 is reflected via the reflector 134 to produce the signal emitted from the sample carrier receiving region 102.

With this variation, both the second source 702 and the power meter 132 respectively move between positions for measuring the power of the signal 704 emitted from the second source 702 and emitting the signal 704 along the collection path 102, and positions in which a sample carrier 104 can be installed in the sample carrier receiving region 102 for processing sample thereon.

The application has been described with reference to various embodiments. Modifications and alterations will occur to others upon reading the application. It is intended that the invention can be construed as including all such modifications and alterations, including insofar as they come within the scope of the appended claims and the equivalents thereof.

What is claimed is:

1. An optical system, comprising:
a sample carrier receiving region configured to receive a sample carrier carrying a sample for processing;
a source that emits an excitation signal having a wavelength within a first predetermined wavelength range along a transmission path;
a first set of optical components that re-directs the excitation signal along an excitation path to the sample carrier receiving region;
a power meter configured to move into and out of the sample carrier receiving region and receive, measure a power of the signal traversing the excitation path in response to the power meter being in the sample carrier receiving region, and generate a signal indicative a power of radiation emitted from the sample carrier receiving region;
a reflector configured to move into and out of the sample carrier receiving and reflect the excitation signal traversing the excitation path in response to the reflector being in the sample carrier receiving region;
a second set of optical components that directs the reflected excitation signal along a collection path; and
a detector configured to detect the excitation signal traversing the collection path and generate a signal indicative of a power of the detected radiation.

2. The system of claim 1, further comprising:
a processor that determines an optical collection efficiency based on a ratio of the signal indicative of the power of the detected radiation to the signal indicative of the power of the radiation emitted from the sample carrier receiving region.

3. The system of claim 2, wherein the processor compares the determined optical collection efficiency with a theoretical optical collection efficiency and generates a signal indicating whether a difference between the determined optical collection efficiency and the theoretical optical collection efficiency satisfies a predetermined optical collection efficiency threshold.

4. The system of claim 3, wherein the theoretical optical collection efficiency is a ratio of a theoretical power of the radiation emitted from the sample carrier receiving region to a theoretical power of the detected radiation.

5. The system of claim 4, further comprising;
determining the theoretical power of the radiation emitted from the sample carrier receiving region as a product of an output power specification of the source and at least one of a transmittance or reflectance specification of the first set of optical components; and
determining the theoretical power of the detected radiation as a product of the theoretical power of the radiation emitted from the sample carrier receiving region and at least one of a transmittance or reflectance specification of the second set of optical components.

6. A method of determining an optical performance of an optical system, comprising:
measuring, with a power meter configured to move into and out of the sample carrier receiving region, a signal power of a signal emitted from a sample carrier receiving by directly measuring an excitation signal traversing an excitation path and received at the sample carrier receiving region;
reflecting, with a reflector configured to move into and out of the sample carrier receiving region, the excitation signal in a direction of a collection path;
measuring a signal power of the signal traversing the collection path and received at a detector, wherein the signal traversing the collection path traverses at least one optical component while traversing the collection path between the sample carrier receiving region and the detector; and
generating a signal indicative of an optical collection efficiency based on a ratio of the signal power of the signal received at the detector to the signal power of the signal emitted from the sample carrier receiving region.

7. The method of claim 6, further comprising:
determining a theoretical optical collection efficiency based on a ratio of a theoretical power of the signal emitted from the sample carrier receiving region to a theoretical power of the signal received at the detector.

8. The method of claim 7, further comprising:
determining an optical collection efficiency performance by comparing a difference value between the measured optical collection efficiency and the theoretical optical collection efficiency with a predetermined optical collection efficiency threshold; and
generating a signal indicating whether the difference value satisfies the predetermined optical collection efficiency threshold.

9. The method of claim 8, further comprising:
determining an optical excitation efficiency performance by comparing a difference value between a measured optical excitation efficiency and a theoretical optical excitation efficiency with a predetermined optical excitation efficiency threshold; and
generating a signal indicating whether the difference value satisfies a predetermined optical excitation efficiency threshold.

10. The method of claim 8, wherein the optical system is part of an apparatus configured to analyze DNA.